US006623491B2

(12) United States Patent
Thompson (10) Patent No.: US 6,623,491 B2
(45) Date of Patent: Sep. 23, 2003

(54) STENT DELIVERY SYSTEM WITH SPACER MEMBER

(75) Inventor: Paul J. Thompson, New Hope, MN (US)

(73) Assignee: ev3 Peripheral, Inc., Plymouth, MN (US)

( * ) Notice: Subject to any disclaimer, the term of this patent is extended or adjusted under 35 U.S.C. 154(b) by 178 days.

(21) Appl. No.: 09/765,719

(22) Filed: Jan. 18, 2001

(65) Prior Publication Data

US 2003/0074043 A1 Apr. 17, 2003

(51) Int. Cl.⁷ .................................................. A61F 11/00
(52) U.S. Cl. ........................................ 606/108; 606/194
(58) Field of Search ................................. 606/108, 194, 606/195, 198; 604/96; 623/1.11

(56) References Cited

U.S. PATENT DOCUMENTS

| | | | |
|---|---|---|---|
| 4,768,507 A | | 9/1988 | Fischell et al. |
| 4,913,141 A | | 4/1990 | Hillstead |
| 5,026,377 A | | 6/1991 | Burton et al. |
| 5,032,113 A | | 7/1991 | Burns |
| 5,279,546 A | * | 1/1994 | Mische et al. ......... 604/101.03 |
| 5,425,712 A | | 6/1995 | Goodin |
| 5,571,086 A | * | 11/1996 | Kaplan et al. ........... 604/96.01 |
| 5,591,172 A | | 1/1997 | Bachmann et al. |
| 5,662,675 A | | 9/1997 | Polanskyj Stockert et al. |
| 5,695,499 A | | 12/1997 | Helgerson et al. |
| 5,755,708 A | * | 5/1998 | Segal ........................... 604/104 |
| 5,759,186 A | | 6/1998 | Bachmann et al. |
| 5,759,191 A | | 6/1998 | Barbere |
| 5,817,102 A | | 10/1998 | Johnson et al. |
| 5,954,729 A | | 9/1999 | Bachmann et al. |
| 6,033,380 A | * | 3/2000 | Butaric et al. ......... 604/103.07 |
| 6,066,157 A | | 5/2000 | Barbere |
| 6,077,295 A | | 6/2000 | Limon et al. |
| 6,120,522 A | | 9/2000 | Vrba et al. |
| 6,129,700 A | * | 10/2000 | Fitz .............................. 604/30 |
| 6,132,460 A | | 10/2000 | Thompson |
| 6,132,461 A | | 10/2000 | Thompson |
| 6,159,228 A | * | 12/2000 | Frid et al. .................... 606/108 |
| 6,190,393 B1 | * | 2/2001 | Bevier et al. ............ 604/96.01 |
| 6,235,050 B1 | * | 5/2001 | Quiachon et al. .......... 623/1.11 |
| 6,306,162 B1 | * | 10/2001 | Patel .......................... 623/1.11 |

FOREIGN PATENT DOCUMENTS

| | | | |
|---|---|---|---|
| EP | 0 839 504 A1 | * | 5/1998 |
| WO | WO 98/24501 | * | 6/1998 |

* cited by examiner

Primary Examiner—Justine R Yu
(74) Attorney, Agent, or Firm—Merchant & Gould P.C.

(57) ABSTRACT

A stent delivery system includes outer and inner elongated, flexible tubular members each having a distal and proximal ends. The outer tubular member is sized to be passed through the body lumen with the distal end advanced to the deployment site and with the proximal end remaining external of the patient's body for manipulation by an operator. The inner tubular member is sized to be received within the outer tubular member. The outer tubular and inner tubular members are axially slideable relative to one another between a transport position and the deploy position. The inner tubular member has a stent attachment location at its distal end. The stent attachment location is covered by the outer tubular member when the inner and outer tubular members are in the transport position. The stent attachment location is exposed when the inner and outer tubular members are in the deploy position. A spacer member is disposed between the inner and outer tubular members. The spacer member maintains spacing between the inner and outer tubular members. Opposing surfaces of the inner and outer tubular members define a first lumen extending from the proximal end towards the distal end of the outer tubular member. An admission port is provided in communication with the first lumen at the proximal end of the outer tubular member. A discharge port is formed through the outer tubular member in communication with the first lumen at the distal end of the outer tubular member.

25 Claims, 8 Drawing Sheets

STENT DELIVERY SYSTEM WITH SPACER MEMBER

I. BACKGROUND OF THE INVENTION

1. Field of Invention

This invention pertains to a system for delivering a stent to a site in a body lumen. More particularly, this invention pertains to a stent delivery system with improved structure between sliding tubular members.

2. Description of the Prior Art

Stents are widely used for supporting a lumen structure in a patient's body. For example, stents may be used to maintain patency of a coronary artery, other blood vessel or other body lumen.

Commonly, stents are commonly metal, tubular structures. Stents are passed through the body lumen in a collapsed state. At the point of an obstruction or other deployment site in the body lumen, the stent is expanded to an expanded diameter to support the lumen at the deployment site.

In certain designs, stents are open-celled tubes which are expanded by inflatable balloons at the deployment site. Other stents are so-called "self-expanding" stents. Self-expanding stents do not use balloons or other application of force to a collapsed stent to cause the expansion of the stent. An example of a self-expanding stent is a coil structure which is secured to a stent delivery device under tension in a collapsed state. At the deployment site, the coil is released so that the coil can expand to its enlarged diameter. Other self-expanding stents are made of so-called shape-memory metals such as nitinol. Such shape-memory stents experience a phase change at the elevated temperature of the human body. The phase change results in expansion from a collapsed state to an enlarged state.

A delivery technique for shape-memory alloy stents is to mount the collapsed stent on a distal end of a stent delivery system. Such a system would include an outer tubular member and an inner tubular member. The inner and outer tubular members are axially slideable relative to one another. The stent (in the collapsed state) is mounted surrounding the inner tubular member at its distal end. The outer tubular member (also called the outer sheath) surrounds the stent at the distal end.

Prior to advancing the stent delivery system through the body lumen, a guide wire is first passed through the body lumen to the deployment site. The inner tube of the delivery system is hollow throughout its length such that it can be advanced over the guide wire to the deployment site.

The combined structure (i.e., stent mounted on stent delivery system) is passed through the patient's lumen until the distal end of the delivery system arrives at the deployment site within the body lumen. The deployment system may include radio-opaque markers to permit a physician to visualize positioning of the stent prior under fluoroscopy to deployment.

At the deployment site, the outer sheath is retracted to expose the stent. The exposed stent is now free to expand within the body lumen. Following expansion of the stent, the inner tube is free to pass through the stent such that the delivery system can be removed through the body lumen leaving the stent in place at the deployment site.

Throughout the procedure, it may be desirable to inject a contrast media (a liquid which can be visualized under fluoroscopy). The contrast media is injected into the space defined between opposing surfaces of the inner and outer tubes. The outer tube has side ports extending through the sidewall of the outer tube near its distal end. The contrast media is injected into the body lumen through the side ports.

Prior art stent delivery systems use inner and outer tubes of generally uniform diameters and circular cross-section throughout their length. This design relies upon the dynamics of fluid flow to retain spacing between the tubes.

In the event the outer diameter of the inner prior art tube is substantially less than the inner diameter of the outer prior art tube, the inner tube could bend relative to the outer tube such that surfaces of the inner tube abut surfaces of the outer tube. As a result, axial forces applied to advance the stent delivery system could be stored in the bent inner tube. Such energy could be suddenly released with sudden and undesired rapid advance or retraction of the distal tip of the tubes when the inner tube straighten. Also, contact between the surfaces of the inner and outer tubes members can result in friction between the members resisting relative moment between the tubes.

The likelihood of the sudden jumping phenomena could be reduced by having the inner and outer tube diameters be as close as possible. However, such close tolerances result in a very small annular gap between the inner and outer tubes which results in increased resistance to flow of contrast media between the inner and outer tube.

Another flaw with prior devices is the absence of comfortable grips to permit the user (such as an interventional cardiologist or a radiologist) to comfortably manipulate the inner tube relative to the outer tube and to readily visualize the relative positioning between the inner tube and outer tubes in their axial alignment.

It is an object of the present invention to provide improved structures for a stent delivery system.

II. SUMMARY OF THE INVENTION

According to a preferred embodiment of the present invention, a stent delivery system is disclosed for delivering a stent to a deployment site in a body lumen of a patient. The stent delivery system includes outer and inner elongated, flexible tubular members each having a distal and proximal ends. The outer tubular member is sized to be passed through the body lumen with the distal end advanced to the deployment site and with the proximal end remaining external of the patient's body for manipulation by an operator. The inner tubular member is sized to be received within the outer tubular member. The outer tubular and inner tubular members are axially slideable relative to one another between a transport position and the deploy position. The inner tubular member has a stent attachment location at its distal end. The stent attachment location is covered by the outer tubular member when the inner and outer tubular members are in the transport position. The stent attachment location is exposed when the inner and outer tubular members are in the deploy position. A spacer member is disposed between the inner and outer tubular members. The spacer member maintains spacing between the inner and outer tubular members. Opposing surfaces of the inner and outer tubular members define a first lumen extending from the proximal end towards the distal end of the outer tubular member. An admission port is provided in communication with the first lumen at the proximal end of the outer tubular member. A discharge port is formed through the outer tubular member in communication with the first lumen at the distal end of the outer tubular member.

IV. DETAILED DESCRIPTION

With reference now to the various drawing figures in which identical elements are numbered identically throughout, a description of a preferred embodiment of the present invention will now be provided.

With initial references to FIGS. 1–4, a stent delivery system 10 is shown. The stent delivery system 10 is for delivery of a stent 12 (schematically shown only in FIG. 2) to a deployment site in a body lumen of a patient's body. By way of non-limiting, representative example, the stent 12 may be a self-expanding, open-celled, tubular stent having a construction such as that shown in U.S. Pat. No. 6,132,461 and formed of a self-expanding, shape-memory or super-elastic metal such as nitinol, or the like. The stent 12 may also be a coil stent or any other self-expanding stent.

The stent 12 is carried on the stent delivery system 10 in a collapsed (or reduced diameter) state. Upon release of the stent 12 from the stent delivery system 10 (as will be described), the stent 12 expands to an enlarged diameter to abut against the walls of the patient's lumen in order to support patency of the lumen.

The stent delivery system 10 includes an inner tubular member 14 and an outer tubular member 16. Both of the inner and outer tubular members 14 and 16 extend from proximal ends 14a, 16a to distal ends 14b, 16b.

The outer tubular member 16 is sized to be axially advanced through the patient's body lumen for the distal end 16b to be placed near the deployment site in the body lumen and with the proximal end 16a remaining external to the patient's body for manipulation by an operator. By way of example, the outer tubular member 16 (also referred to as a sheath) may be a braid-reinforced polyester of tubular construction to resist kinking and to transmit axial forces along the length of the sheath 16. The outer tubular member 16 may be of widely varying construction to permit varying degrees of flexibility of the outer tubular member 16 along its length.

The proximal end 16a of the outer tubular member 16 is bonded to a manifold housing 20. The manifold housing 20 is threadedly connected to a lock housing 22. A strain relief jacket 24 is connected to the manifold housing 20 and surrounds the outer tubular member 16 to provide strain relief for the outer tubular member 16.

Figure 5:
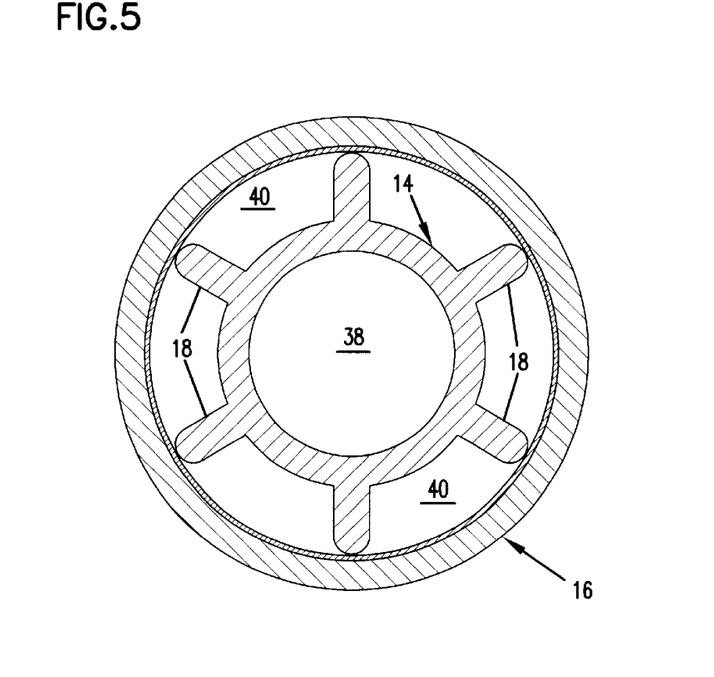
FIG. 5 is a cross-sectional view of the inner and outer tubular members of the stent delivery system of FIG. 1 taken along lines 5—5 of FIG. 3.

The inner tubular member 14 is preferably formed of nylon but may be constructed of any suitable material. Along a portion of its length from the proximal end 16a of the outer tubular member 16 to a stent attachment location 26 (shown in FIG. 2), the inner tubular member 14 is a cylinder with a spacer member 18 which, in a preferred embodiment, comprises radially projecting and axially extending splines 18 (best shown with reference to FIGS. 3 and 5). The function and purpose of the splines 18 will be described later.

Figure 1:
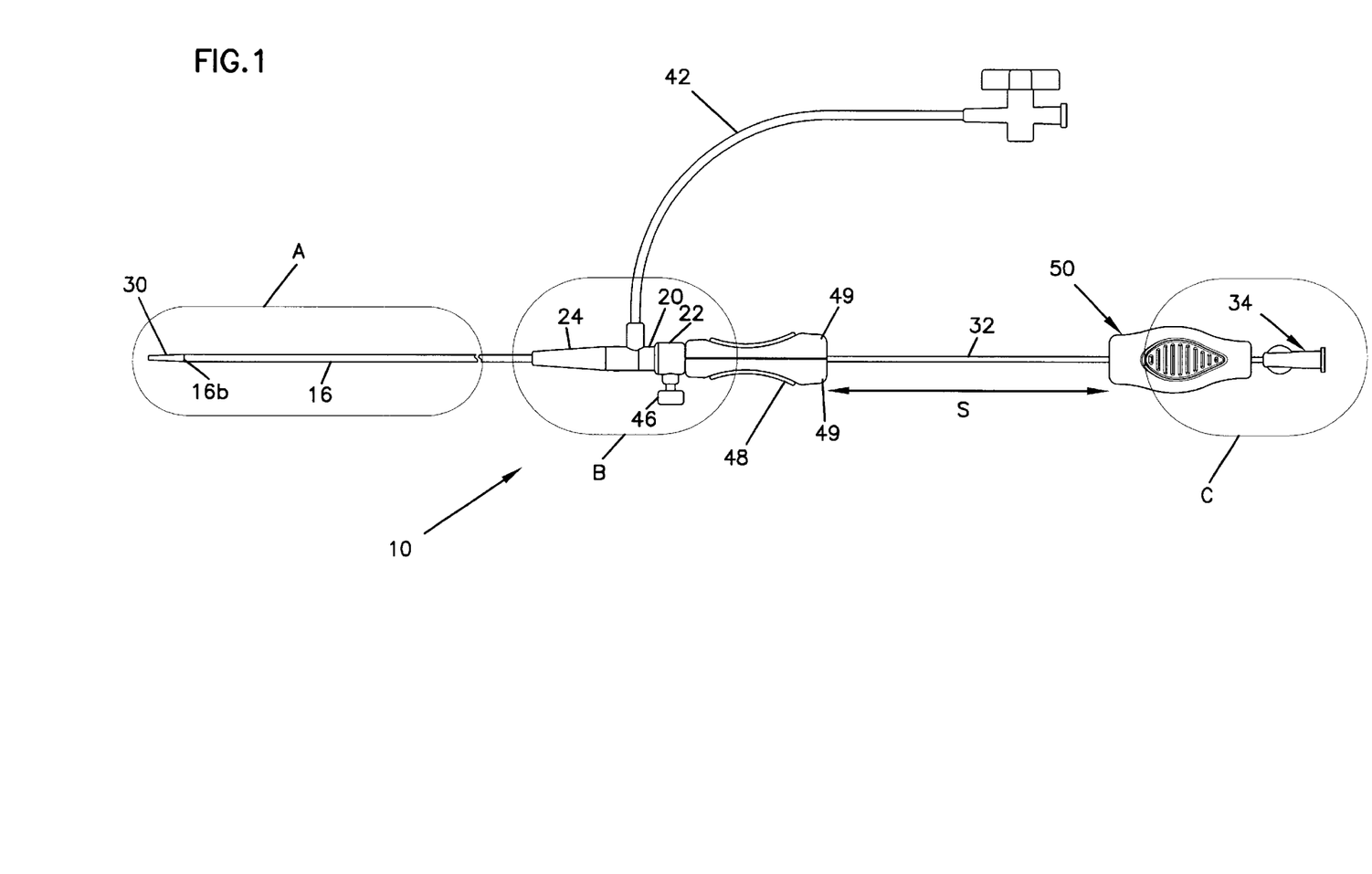
FIG. 1 is a side elevation view of a stent delivery system according to the present invention.
Figure 2:
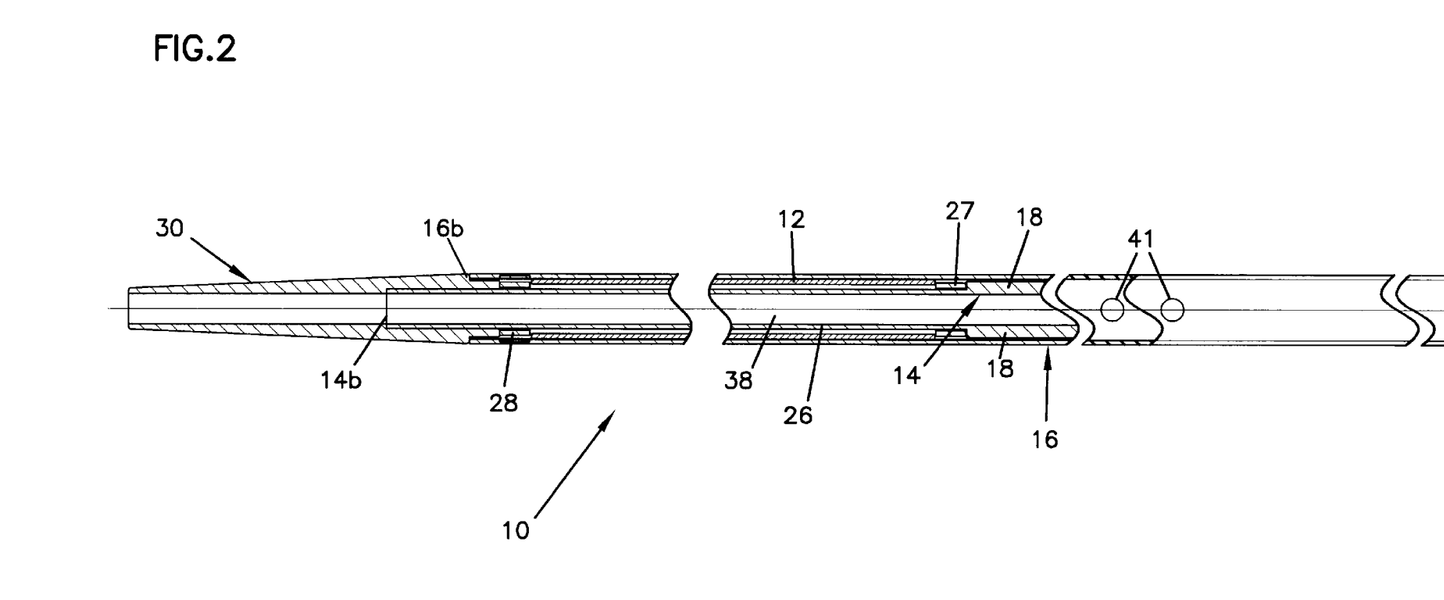
FIG. 2 is a side sectional view of a distal end of the stent delivery system of FIG. 1, shown in FIG. 1 as Detail A.

At the distal end 14b of the inner tubular member 14, the inner tubular member 14 has no splines. The splineless length of the distal end of the inner tubular member 14 is of sufficient length to be greater than an axial length of the stent 12. This distal splineless length of the inner tubular member defines the stent attachment location 26 between spaced apart radio-opaque markers 27, 28 which are attached to the inner tubular member 14. The radio-opaque markers 27, 28 permit a physician to accurately determine the position of the stent attachment location 26 within the patient's lumen under fluoroscopy visualization. A tapered and flexible distal tip member 30 is secured to the reduced and splineless portion of the inner tubular member 14. The highly flexible distal tip member 30 permits advancement of the stent deployment system 10 through the patient's lumen and minimizes trauma to the walls of the patient's lumen.

Figure 3:
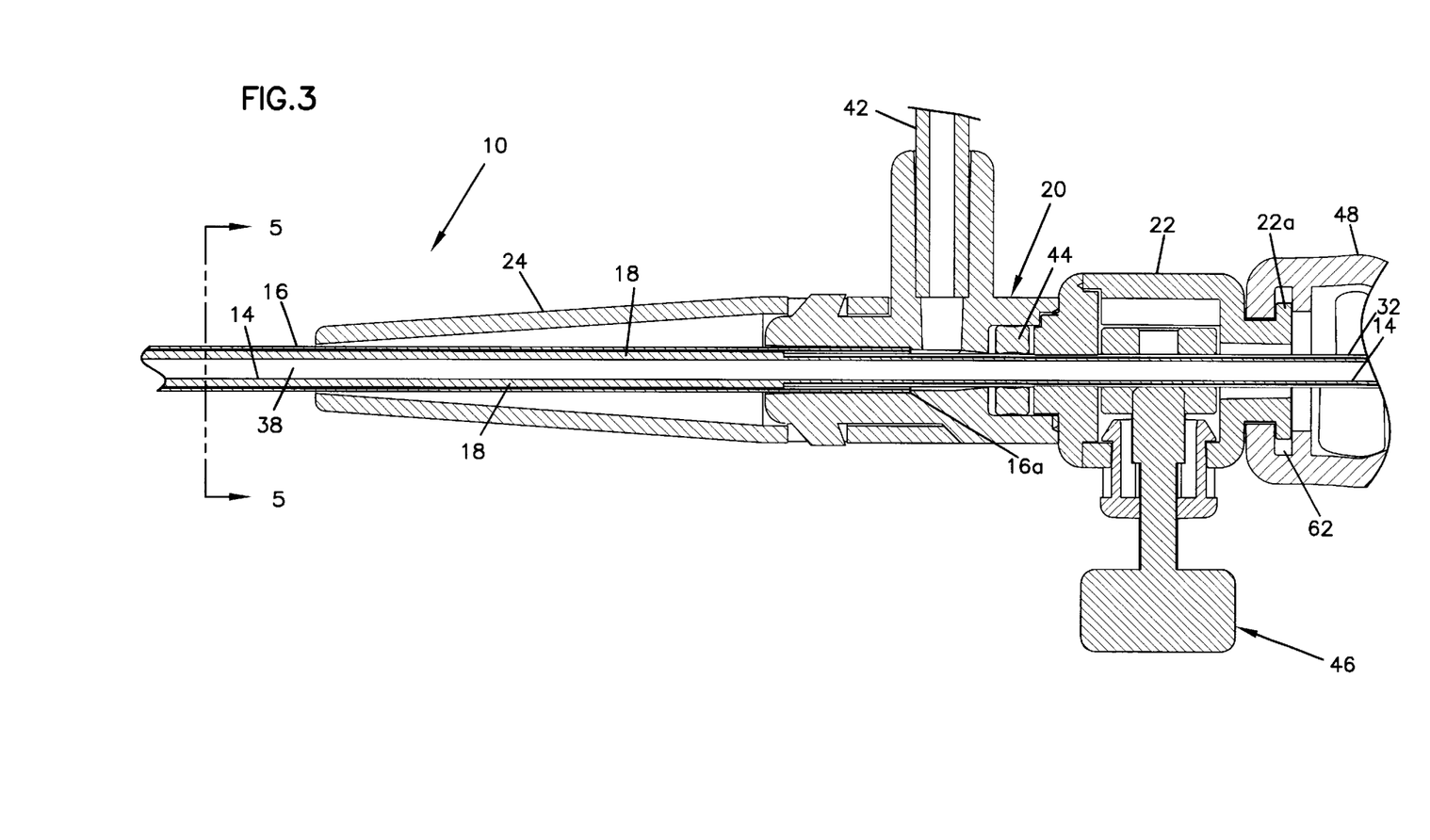
FIG. 3 is a side sectional view of a proximal end of the stent delivery system of FIG. 1, shown in FIG. 1 as Detail B.
Figure 4:
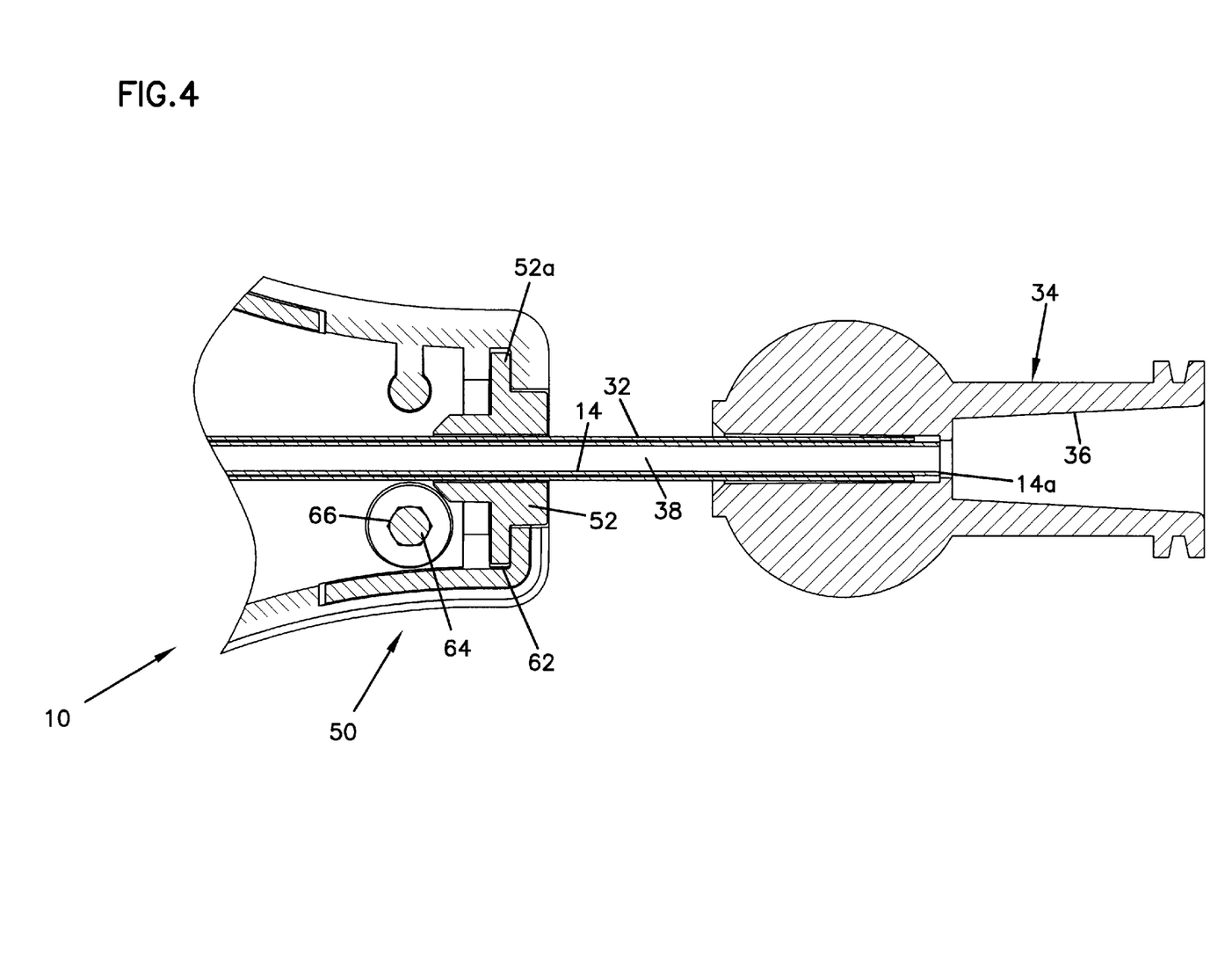
FIG. 4 is a sectional view of a second handle of the stent delivery system of FIG. 1 and showing, in section, a guide wire port, shown in FIG. 1 as Detail C.

As best shown in FIGS. 3 and 4, from the proximal end 16a of the outer tube 16 to the inner tube proximal end 14a, the inner tube 14 is cylindrical and splineless. The inner tube 14 passes through both the manifold housing 20 and lock housing 22. A stainless steel jacket 32 surrounds and is bonded to the inner tubular member 14 from the proximal end 14a up to and abutting the splines 18.

At the inner tube proximal end 14a, a port housing 34 is bonded to the stainless steel jacket 32. The port housing 34 has a tapered bore 36 aligned with an inner lumen 38 of the tubular member 14. The inner lumen 38 extends completely through the inner tubular member 14 so that the entire delivery system 10 can be passed over a guide wire (not shown) initially positioned within the patient's lumen. Opposing surfaces of the inner and outer tubular members 14 and 16, define a first lumen 40 (best seen in FIG. 5).

The manifold housing 20 carries an admission port 42 for injecting a contrast media into the interior of the manifold housing 20. The interior of the manifold housing 20 is in fluid flow communication with the first lumen 40. Discharge ports 41 are formed through the outer tubular member 16 to permit contrast media to flow from the first lumen 40 into the patient's body lumen.

An O-ring 44 surrounds the stainless steel jacket 32 between the manifold housing 20 and lock housing 22. Upon threaded connection of the manifold housing 20 to the lock housing 22, the O-ring 44 compresses against the stainless steel jacket 32 in sealing engagement to prevent contrast media from flowing in any path other than through the first lumen 40.

The lock housing 22 carries a threaded locking member (or lock nut) 46 which can be turned to abut the stainless steel jacket 32. The lock nut 46 can be released to free the stainless steel jacket to move axially. According, when the lock nut 46 engages the jacket 32, the jacket 32 (and attached inner tubular member 14) cannot move relative to the lock housing 22, manifold housing 20 or the outer tubular member 16. Upon release of the lock nut 46, the inner tubular member 14 and outer tubular member 16 are free to slide axially relative to one another between a transport position and a deploy position.

First and second handles 48, 50 are secured to the lock housing 22 and jacket 32, respectively. In the transport position, the handles 48, 50 are spaced apart and the outer tubular member 16 covers the stent attachment location 26 to prevent premature deployment of the stent 12. When the handle 48 is pulled rearwardly toward the handle 50, the outer tubular member 16 slides rearwardly or proximally relative to the inner tubular member 14. Preferably, the outer tubular member 16 slides rearwardly a distance sufficient to fully expose the stent attachment location 26 and permit the stent 12 to freely expand toward its fully expanded diameter. After such expansion, the stent delivery system can be proximally withdrawn through the expanded stent and removed.

The first handle 48 is rotatably mounted on a flange 22a of the lock housing 22. The first handle 48 surrounds the stainless steel jacket 32 and is freely rotatable about the longitudinal axis of the jacket 32 and freely rotatable about the flange 22a. The first handle 48 is axially affixed to the lock housing 22 such that axially forces applied to the first handle 48 are transmitted through the lock housing 22 and manifold housing 20 to the outer tubular member 16 to axially move the outer tubular 16. However, rotary action of the first handle 48 about the axis of the stainless steel jacket 32 is not transmitted to the housings 20, 22 or to the outer tubular member 16 by reason of the free rotation of the first handle 48 on flange 22a.

The second handle 50 is mounted on an anchor 52 which is bonded to the stainless steel jacket 32 through any suitable means (such as by use of adhesives). The anchor 52 includes a flange 52a which is radial to the axis of the stainless steel jacket 32. The second handle 50 is mounted on the flange 52a and is free to rotate on the anchor 52 about the axis of the stainless steel jacket 32. However, axial forces applied to the handle 50 are transmitted to the stainless steel jacket 32 which, being bonded to the inner tubular member 14, results in axial movement of the inner tubular member 14.

With the handle construction described above, relative axial movement between the handles 48, 50 results in relative axial movement between the inner and outer tubular members 14, 16. Rotational movement of either of the handles 48, 50 does not affect rotational positioning of the inner or outer tubular members 14, 16 and does not affect axial positioning of the inner and outer tubes 14, 16.

The free rotation of the handles 48, 50 results in ease of use for a physician who may position his or her hands as desired without fear of interfering with any axial positioning of the inner and outer tubular members 14, 16. The spacing between the handles 48, 50 is equal to the stroke between the transport position and the deploy position of the tubular members 14, 16. As a result, the spacing permits the operator to have ready visual indication of the relative axial positioning between the inner and outer tubular members 14, 16. This relative axial positioning can be fixed by engaging the lock nut 46. In any such positioning, contrast media can be injected through the admission port 42 into the chamber 40 with the contrast media flowing out of the side ports 41 into the body lumen to permit visualization under fluoroscopy.

Figure 6:
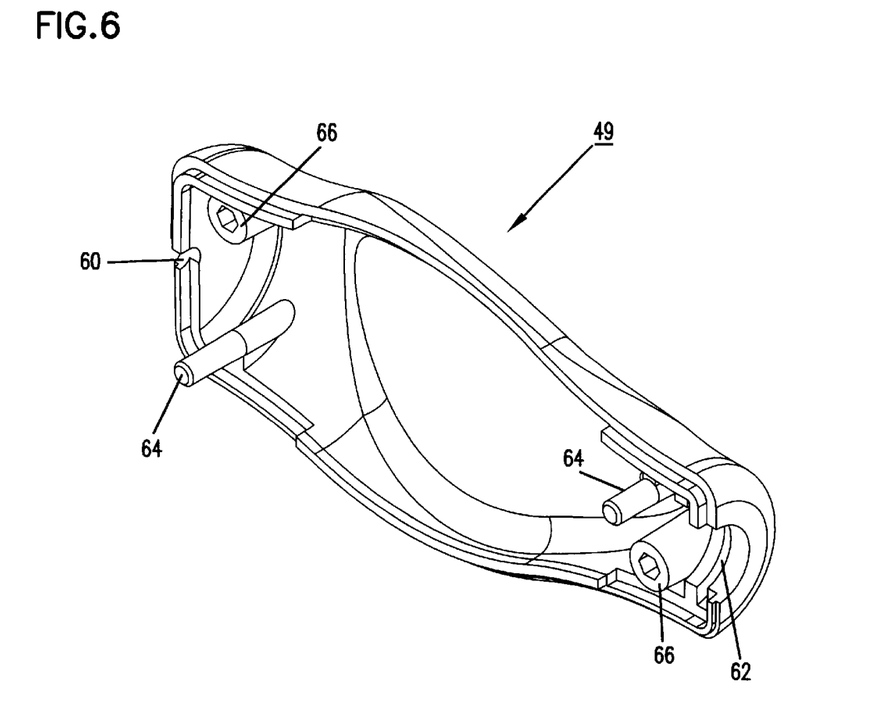
FIG. 6 is a perspective view of one-half of a handle of the stent delivery system of FIG. 1 with the opposite half being of identical construction.

With reference to FIG. 6, each of the handles 48, 50 is formed of identical halves 49 (FIG. 6) of injected molded plastic to permit ease of manufacture. When the handle halves 49 are joined together, pins 64 are received in aligned openings 66 of an opposing half 49 for attachment and permanent connection of two halves 49. The halves 49 include first openings 60 proximate to the outer diameter of the stainless steel jacket 32. At opposite ends, the halves 49 include annular recesses 62 to receive either of flanges 22a or 52a for rotatable attachment upon joinder of two halves 49.

In the preferred embodiment shown, the splines 18 are radially projecting and extend substantially the entire axial length of the inner tubular member 14 between the proximal end 16b of the outer tubular member 16 and the proximal radio-opaque marker 27. The radial dimension and axial length of each of the splines 18 is identical and, in a preferred embodiment, all splines 18 have a continuous uninterrupted length. However, it will be appreciated that the radial dimensions need not be identical and the splines 18 need not have an uninterrupted length. Instead, the splines 18 are an example of an embodiment of a spacer member used to maintain a spacing between the outer tubular member 16 and inner tubular member 14.

The spacer member 18 keeps the inner tubular member 14 in concentric alignment with the outer tubular member 16. This permits the use of a very small diameter inner tubular member 14 relative to the diameter of the outer tubular member 16 to increase the volume of the first lumen 40. This reduces any impediment to flow of contrast media through the first lumen 40 and increases the volume of contrast media within the first lumen 40.

By reason of the splines 18, the inner tubular member 14 cannot bend relative to the outer tubular member 16 thereby avoiding the problems associated with the prior art designs as previously discussed. Also, since the splines 18 contact the outer tubular member 16 only at small surface areas along the length, very small friction results from sliding motion between the inner and outer tubular members 14, 16.

With stent deployment systems having premounted stents of various axial lengths, the positioning of the second handle 50 on the stainless steel jacket 32 can be selected at time of assembly so that a spacing S (see FIG. 1) between the handles 48, 50 corresponds to the length of the stent 12 carried on the stent deployment system. For example, in a preferred embodiment, the spacing S is about 10 millimeters longer than the deployed length of the stent. Accordingly, the user will know that the outer tubular member 16 has been fully retracted when the handles 48, 50 have been pushed completely together to completely release the stent 12. Also, the freely rotatable handles 48, 50 are easy to hold from any angle without slippage. The lock nut 46 ensures that the stent 12 will not deploy prematurely.

Figure 7A:
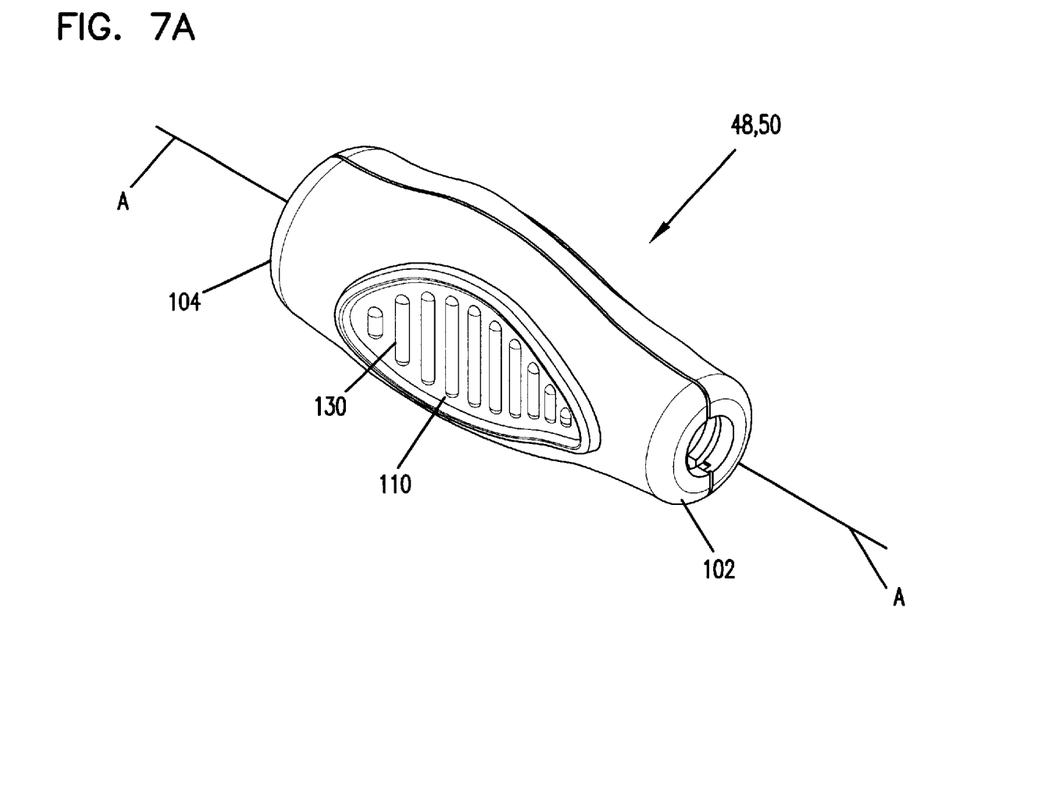
FIG. 7A is a perspective view of one of the handles of the stent delivery system of FIG. 1.
Figure 7B:
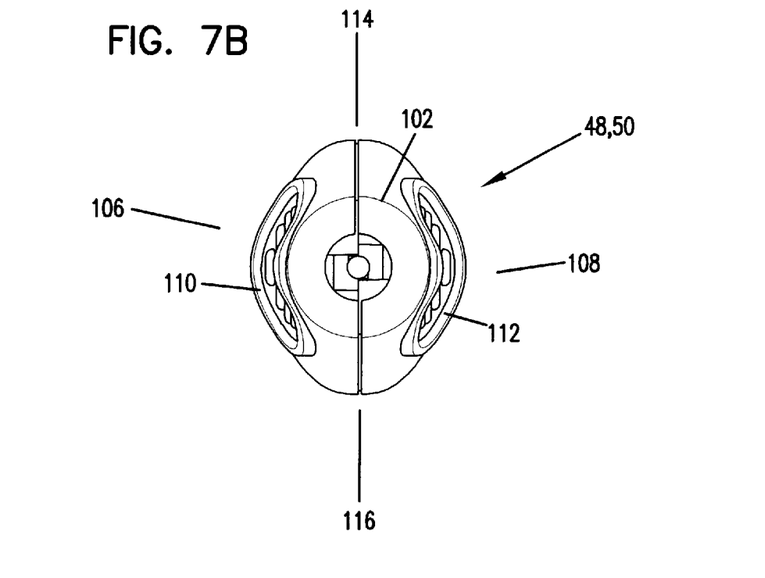
FIG. 7B is a front end view of the handle of FIG. 7A.
Figure 7C:
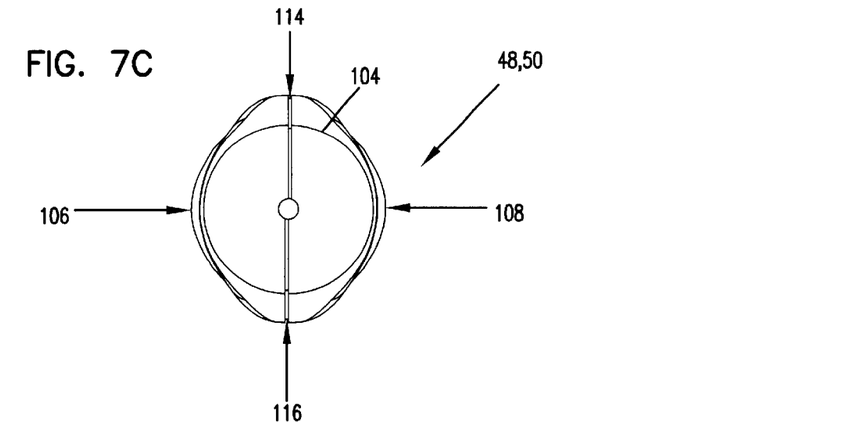
FIG. 7C is a back end view of the handle of FIG. 7A.
Figure 7D:
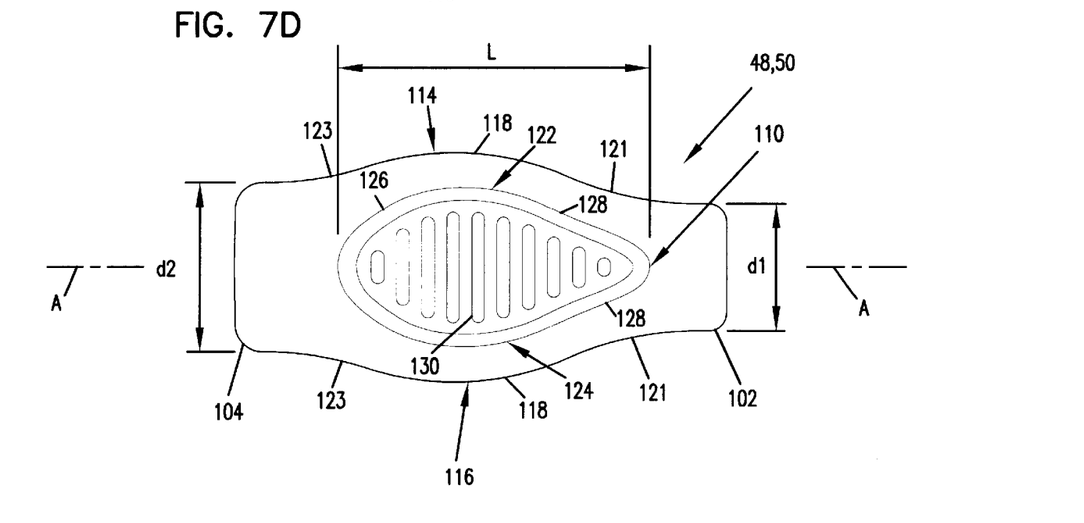
FIG. 7D is a front side view of the handle of FIG. 7A.

FIGS. 7A–7G show one of the handles 48, 50 in isolation from the delivery system 10. The depicted handle 48, 50 is elongated along a central axis A—A and includes a first end 102 positioned opposite from a second end 104. The first end 102 preferably has a smaller perimeter (i.e., circumference) than the second end 104. For example, as shown in FIG. 7D, the first end preferably has a radial dimension d1 (i.e., the diameter of the first end 102) that is smaller than a radial dimension d2 of the second end 104 (i.e., the diameter of the second end 104). Preferably, the ends 102 and 104 have a generally round perimeter.

Figure 7E:
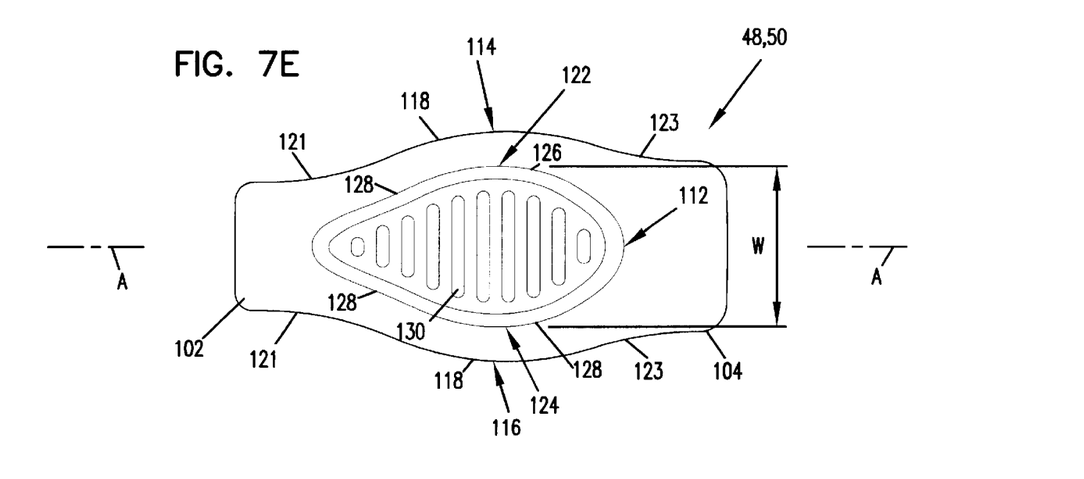
FIG. 7E is a back side view of the handle of FIG. 7A.
Figure 7F:
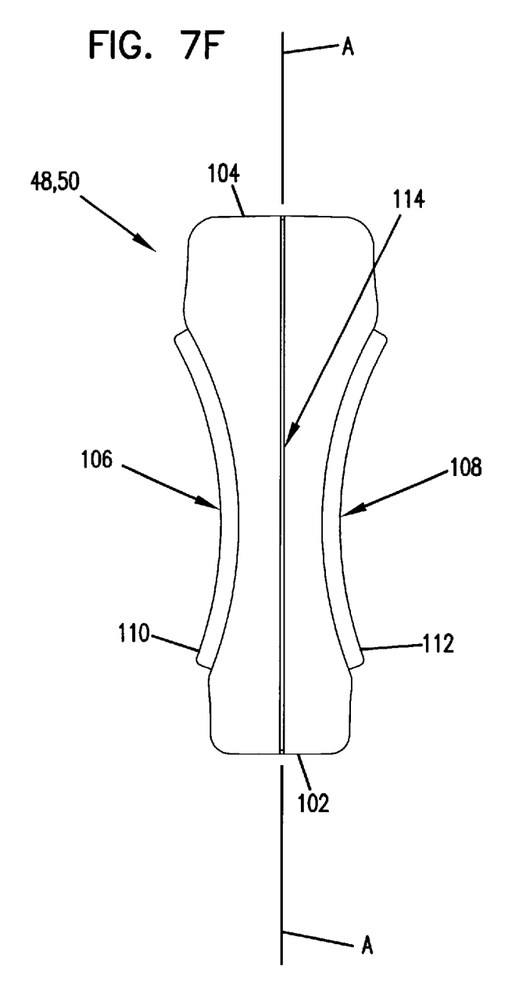
FIG. 7F is a top view of the handle of FIG. 7A.
Figure 7G:
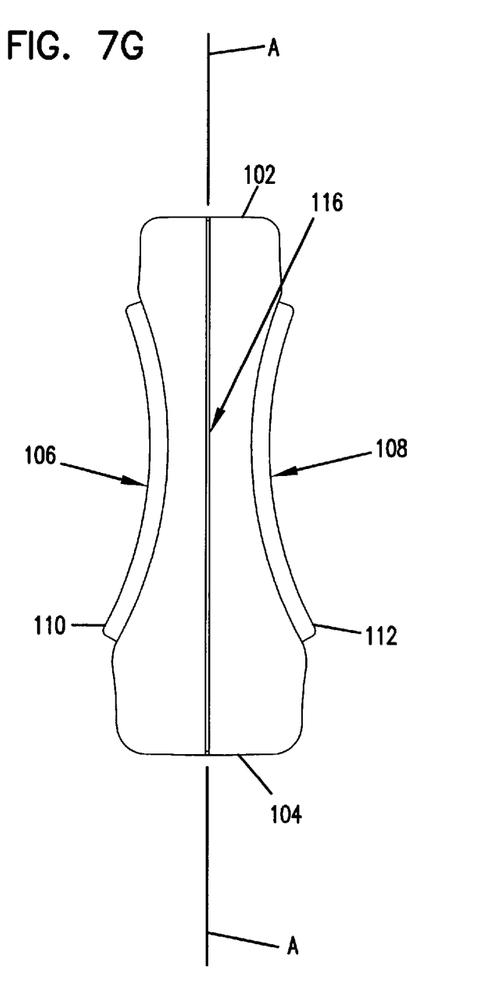
FIG. 7G is a bottom view of the handle of FIG. 7A.

Referring to FIGS. 7F and 7G, the handle 48, 50 also includes first and second sides 106 and 108 that extend longitudinally between the first and second ends 102 and 104. The first and second sides 106 and 108 preferably face in opposite directions. Concave gripping regions 110 and 112 are located at the first and second sides 106 and 108. The concave gripping regions 110 and 112 each define a concave curvature as the gripping regions 110, 112 extend in a longitudinal direction (i.e., along axis A—A) between the first and second ends 102 and 104.

Referring to FIGS. 7D and 7E, the handle 48, 50 also includes third and fourth sides 114 and 116 that extend longitudinally between the first and second ends 102 and 104. The third and fourth sides 114 and 116 face in opposite directions, and extend circumferentially (about the axis A—A) between the first and second sides 106 and 106. Preferably, the third and fourth sides 114 and 116 include convex regions 118 that extend in a longitudinal direction along an intermediate region of the handle 48, 50, and concave regions 121 and 123 that extend from the convex regions to the ends 102 and 104 of the handle 48, 50. The third and fourth sides 114 and 116 also define a convex curvature that extends in a circumferential direction (i.e., about the axis A—A as best shown in FIGS. 7B and 7C).

Referring again to FIGS. 7D and 7E, a length L of the concave gripping regions 110, 112 is preferably shorter than a total length of the handle 48, 50. Also, the gripping regions 110, 112 are preferably generally centered along the total length of the handle 48, 50. Additionally, the regions 110, 112 preferably include top and bottom edges 122 and 124 having convex curvatures 126 that transition into concave curvatures 128 adjacent the first end 102. The regions 110, 112 preferably have a maximum transverse width W at an intermediate position along their lengths L. The width W is preferably measured in a direction transverse relative to the axis A—A. The regions 110, 112 also preferably include elongated gripping projections 130. The gripping projections 130 are preferably parallel to one another, and preferably extend in a transverse direction relative to the axis A—A. The projections 130 are preferably longer at the intermediate positions of the gripping regions 110, 112 than adjacent the ends of the gripping regions 110, 112. In one non-limiting embodiment, the main body of the handle 48, 50 is made of a relatively hard material (e.g., polybutylene terephthalate) and the gripping regions 110, 112 are made of a softer, more resilient material (e.g., an overmolded polyester elastomer).

It has been shown how the objects of the invention have been attained in a preferred manner. Modifications and equivalents of the disclosed concepts are intended to be included within the scope of the claims.

What is claimed is:

1. A stent delivery system for delivering a stent to a deployment site in a body lumen of a patient's body, said stent delivery system comprising:
   an elongated, flexible, outer member having a distal end and a proximal end, the outer member having a wall that defines a first lumen;
   an elongated, flexible, inner member having a distal end and a proximal end, the inner member having a wall that defines a second lumen;
   said outer member sized to be passed through said body lumen with said distal end advanced to said deployment site and with said proximal end external to said body for manipulation by an operator;
   said inner member received within said outer member with said inner member and said outer member axially slideable relative to one another between a transport position and a deploy position;
   said inner member having a stent attachment location at said distal end of said inner member, said stent attachment location covered by said outer member when said inner and outer members are in said transport position, said stent attachment location exposed when said inner and outer members are in said deploy position;
   a fluid passage defined between said wall of said inner member and said wall of said outer member;
   a plurality of circumferentially spaced apart spacer structures disposed along a majority of the length of the fluid passage between said wall of said inner member and said wall of said outer member with said spacer structures spacing said wall of said inner member from said wall of said outer member;
   an admission port in communication with said fluid passage; and
   a discharge port in communication with said fluid passage at a location axially spaced from the admission port.

2. A stent delivery system according to claim 1 wherein said spacer structures extend substantially an entire length from said proximal end of said outer member to said stent attachment location.

3. A stent delivery system according to claim 1 wherein said spacer structures are disposed to maintain said inner member centrally positioned within said outer member.

4. A stent delivery system according to claim 1 wherein said spacer structures include a plurality of splines carried on said wall of said inner member and extending radially outwardly towards said outer member and extending linearly along a length of said inner member.

5. A stent delivery system according to claim 1 wherein said second lumen allows said inner member to track over a guide wire.

6. A stent delivery system according to claim 1 further comprising a stent carried at said stent attachment location.

7. A stent delivery system according to claim 1 further comprising a first handle rotatably connected to said proximal end of said outer member.

8. A stent delivery system according to claim 7 further comprising a second handle rotatably connected to said proximal end of said inner member.

9. A stent delivery system according to claim 1 comprising a locking member for fixing a relative axial position between said inner member and said outer member.

10. A stent delivery system according to claim 1, wherein the spacer structures include a plurality of splines.

11. A stent delivery system according to claim 10, wherein the splines are integral with the wall of the inner member.

12. A stent delivery system according to claim 10, wherein the splines include base ends connected to one of the walls of the inner and outer members, and tip ends that engage the other of the walls of the inner and outer members.

13. A stent delivery system according to claim 12, wherein the base ends of the splines are integral with the wall of the inner member.

14. A stent delivery system according to claim 12, wherein the tips of the splines are narrower than the bases of the splines.

15. A stent delivery system according to claim 12, wherein the tips of the splines are rounded.

16. A stent delivery system for delivering a stent to a deployment site in a body lumen of a patient's body, said stent delivery system comprising:
   an elongated, flexible, outer member having an outer member length and an inner surface that defines a lumen;
   an elongated, flexible, inner member having an inner member length and positioned within the lumen of the outer member, the inner member and the outer member axially slideable relative to one another between a transport position and a deploy position, the inner member including a main body;

the outer member being sized to be passed through the body lumen;

the inner member having a stent mounting location that is covered by the outer member when the inner and outer members are in said transport position, the stent mounting location exposed when said inner and outer members are in the deploy position; and a plurality of circumferentially spaced apart spacer structures that extend between the main body of the inner member and the inner surface of the outer member the spacer structures being coextensive with a majority of the lengths of the inner and outer members.

17. The stent delivery system according to claim 16, wherein the stent delivery system further comprises a plurality of handles, wherein the plurality of handles is configured to respond to axial movements in the plurality of handles with a corresponding axial movement in the inner and outer members, and the plurality of handles is further configured to not affect the rotational position of the inner and outer members.

18. A stent delivery system according to claim 17, further comprising:

a fluid passage defined between the main body of the inner member and the inner surface of the outer member, an admission port in communication with the fluid passage, and a discharge port in communication with the fluid passage at a location axially spaced from the admission port.

19. A stent delivery system according to claim 17, wherein the spacer structures include base ends connected to one of the main body of the inner member and the inner surface of the outer member, and tip ends that engage the other of the main body of the inner member and the inner surface of the outer member.

20. A stent delivery system according to claim 19, wherein the base ends of the spacer structures are integral with the main body of the inner member.

21. A stent delivery system according to claim 20, wherein the tips of the spacer structures are narrower than the bases of the spacer structures.

22. A stent delivery system according to claim 19, wherein the tips of the spacer structures are rounded.

23. A stent delivery system according to claim 19, wherein the spacer structures prevent the main body of the inner member from moving radially within the lumen of the outer member such that a cross-sectional area of the fluid passage is maintained by the spacer structures when the inner and outer members are bent.

24. A catheter device comprising:

an elongated, flexible, outer member having an inner surface that defines a first lumen;

an elongated, flexible, inner member positioned within the first lumen, the inner member including a main body;

the outer member being sized to be passed through a body lumen; and a plurality of circumferentially spaced apart spacer structures that extend between the main body of the inner member and the inner surface of the outer member for maintaining a spacing between the main body of the inner member and the inner surface of the outer member, the circumferentially spaced apart spacer structures being present along a majority of a length of the catheter device.

25. The catheter device of claim 24, wherein each of the spacer structures has an uninterrupted length that extends along a majority of the length of the catheter device.

* * * * *

UNITED STATES PATENT AND TRADEMARK OFFICE
CERTIFICATE OF CORRECTION

PATENT NO. : 6,623,491 B2
DATED : September 23, 2003
INVENTOR(S) : Thompson

It is certified that error appears in the above-identified patent and that said Letters Patent is hereby corrected as shown below:

<u>Title page,</u>
Item [56], References Cited, FOREIGN PATENT DOCUMENTS, please remove both the asterisks in both references.

<u>Column 6,</u>
Line 55, "dimension dl" should read -- dimension d1 --

<u>Column 9,</u>
Line 10, "outer member the" should read -- outer member, the --
Line 21, "according to claim 17," should read -- according to claim 16, --
Line 30, "according to claim 17," should read -- according to claim 18, --

<u>Column 10,</u>
Line 4, "according to claim 20," should read -- according to claim 19, --
Line 23, "according to claim 19," should read -- according to claim 18, --

Signed and Sealed this

Twenty-fifth Day of January, 2005

JON W. DUDAS
*Director of the United States Patent and Trademark Office*